United States Patent
Agarwal

(10) Patent No.: US 9,055,915 B2
(45) Date of Patent: Jun. 16, 2015

(54) DEVICE FOR EXTERNALLY MARKING THE LOCATION OF ORGANS ON SKIN DURING A CAT SCAN

(71) Applicant: Ghansham D. Agarwal, Kolkata (IN)

(72) Inventor: Ghansham D. Agarwal, Kolkata (IN)

( * ) Notice: Subject to any disclaimer, the term of this patent is extended or adjusted under 35 U.S.C. 154(b) by 0 days.

(21) Appl. No.: 14/329,317

(22) Filed: Jul. 11, 2014

(65) Prior Publication Data

US 2014/0321622 A1    Oct. 30, 2014

Related U.S. Application Data

(63) Continuation of application No. PCT/IN2013/000414, filed on Aug. 8, 2013, and a continuation-in-part of application No. 13/601,170, filed on Aug. 31, 2012.

(30) Foreign Application Priority Data

Jul. 10, 2012    (IN) .............................. 764/KOL/2012

(51) Int. Cl.
| | |
|---|---|
| *A61B 6/00* | (2006.01) |
| *A61B 6/12* | (2006.01) |
| *A61B 19/00* | (2006.01) |
| *A61B 6/04* | (2006.01) |
| *A61N 5/10* | (2006.01) |
| *A61B 17/00* | (2006.01) |
| *A61B 6/03* | (2006.01) |

(52) U.S. Cl.
CPC ................. *A61B 6/48* (2013.01); *A61B 6/0492* (2013.01); *A61B 6/12* (2013.01); *A61N 5/1049* (2013.01); *A61B 19/54* (2013.01); *A61B 2017/00946* (2013.01); *A61B 2019/206* (2013.01); *A61B 2019/207* (2013.01); *A61B 2019/5287* (2013.01); *A61B 2019/5466* (2013.01); *A61B 6/032* (2013.01)

(58) Field of Classification Search
USPC ............... 378/204, 207, 208, 210; 250/505.1, 250/515.1, 516.1
See application file for complete search history.

(56) References Cited

U.S. PATENT DOCUMENTS

| | | | |
|---|---|---|---|
| 4,838,265 A | 6/1989 | Cosman et al. | |
| 4,918,715 A | 4/1990 | Krupnick et al. | |
| 5,052,035 A * | 9/1991 | Krupnick | 378/163 |
| 5,193,106 A * | 3/1993 | DeSena | 378/163 |
| 5,260,985 A | 11/1993 | Mosby | |
| 6,041,094 A | 3/2000 | Russell | |
| 6,138,302 A | 10/2000 | Sashin et al. | |
| 6,356,621 B1 | 3/2002 | Furumori et al. | |
| 7,853,311 B1 * | 12/2010 | Webb | 600/426 |

(Continued)

FOREIGN PATENT DOCUMENTS

WO    WO-2011094833 A1    8/2011

OTHER PUBLICATIONS

International Search Report of PCT/IN2013/000414 mailed Nov. 29, 2013.

*Primary Examiner* — David A Vanore
(74) *Attorney, Agent, or Firm* — Venable LLP; Keith G. Haddaway; David M. Klecyngier

(57) ABSTRACT

A novel device for marking location of organs on skin as per CAT scan comprising of a sheet having a plurality of vertical, horizontal and oblique lines wherein the sheet is provided in the form of a mesh. The device can be used for radiotherapy of head to localize point of radiotherapy, for other parts of body to localize/mark organs on skin after CAT scan and also for surgery of Brain to localize tumors.

16 Claims, 5 Drawing Sheets

(56) References Cited

U.S. PATENT DOCUMENTS

| | | | |
|---|---|---|---|
| 7,902,816 B2 * | 3/2011 | Shechter | 324/207.12 |
| 8,487,287 B2 * | 7/2013 | Cadwalader et al. | 250/515.1 |
| 8,699,670 B2 * | 4/2014 | Graumann et al. | 378/162 |
| 2011/0093108 A1 * | 4/2011 | Ashby et al. | 700/103 |
| 2014/0056495 A1 * | 2/2014 | Janssens | 382/128 |

* cited by examiner

DEVICE FOR EXTERNALLY MARKING THE LOCATION OF ORGANS ON SKIN DURING A CAT SCAN

CROSS REFERENCE TO RELATED APPLICATIONS

This application is a continuation of PCT International Application No. PCT/IN2013/000414, filed, Jul. 8, 2013, which claims the benefit of Indian Application No. 764/KOL/2012, filed Jul. 10, 2012. This application is also a continuation-in-part of U.S. application Ser. No. 13/601,170, filed Aug. 31, 2012, which is pending.

FIELD OF INVENTION

This invention relates to a novel device for externally marking the location of organs on skin during a CAT scan.

BACKGROUND

In today's medical world Computerized Tomography scanning (a CT or CAT scan) is known to be very common investigation procedure, which provides a cross sectional view of the body. CAT scans are used to locate organs and anatomical features or abnormalities such as lesions and tumors within the organs Conventional X-ray generates only two dimensional flat view of organs. However, use of a CAT scan provides for viewing of organs in three dimensional form as well.

For planning a medical procedure such as surgical operation or radiation therapy, identifying the location of anatomical features such as organs, defects, lesions or tumors by reference to a location on the surface of the body (skin) is very important.

There are several methods for marking the location of organs externally on skin. The oldest and most common method involves identifying body landmarks from which the distance to organs is calculated, followed by marking the location. However such method has its own possibility of errors.

Another method involves the use of radio-opaque markings on skin followed by CAT scan. However, it may need multiple scan to delineate an organ with the possibilities of errors. This is because the exact position of the organ cannot be located accurately just by placing the marker randomly. Thus, there are fair chances of involvement of the errors.

Another method involves carrying out the CAT scan with sheets comprising of oblique radio-opaque lines. In this method, the resultant image must be processed through a special computer program and translated on to specialized equipment called stereo-tactic device. Thus, the drawback associated with this method include that it requires special computer program and stereo-tactic frame (equipment), which is very expensive and requires special training.

Hence, there is a need to develop a novel device for marking location of organs on skin as per CAT scan to assist medical persons, which can address the aforesaid problems. In particular, such devices should not require the use of expensive specialized equipment so that it is more readily available. The device and method should also result in accurate and reproducible CAT scans. With the help of this device a medical person can easily mark on skin location of organs as per CAT scan.

SUMMARY OF THE INVENTION

The primary object of the present invention is to provide a novel device for externally marking the location of organs on skin during a CAT scan.

Another object of the present invention is to provide a novel device for externally marking the location of organs on skin during a CAT scan which is efficient and reliable.

According to this invention, there is provided a novel device for marking on skin the location of organs and anatomical features identified in a CAT scan. The device is a flexible sheet having a plurality of lines wherein the sheet comprises an x-ray opaque material, for example barium sulphate, and is provided in the form of a mesh. The sheet can be made of soft bendable plastic such as low density polyethylene. The lines can be a series of vertical, horizontal and/or oblique lines. The vertical lines and/or the oblique lines may be thicker than the horizontal lines. The vertical lines can be arranged in a pattern of thick and thin lines at regular intervals, for example every fifth vertical line can be thicker than the intervening vertical lines. The x-ray opaque material may be is impregnated within or coated on the flexible sheet.

This invention also discloses another type of craniomapper, which is called craniomapper coronal. This is used for obtaining coronal section. So that, location of lesions in vertex area can be marked.

The invention is also a method of identifying the location of an internal anatomical feature during a CAT scan comprising placing the flexible sheet on a surface of the body, performing the CAT scan; identifying the internal anatomical feature to be located; and identifying the location of the anatomical feature by reference to the position on the flexible sheet.

The anatomical feature can be, for example, an organ, a defect, a lesion or a tumor. The surface of the body to which the sheet is applied can be the head.

The invention thus provides a device for marking location of organs on skin as per CAT scan which is simple to use by common medical persons.

The invention has the advantage of marking location of organs on skin as per CAT scan which is cost effective. In addition, the device is easy to use and convenient to manufacture.

According to this invention, there is provided a device for identifying the location of internal anatomical features by externally marking on skin during a CAT scan comprising a flexible sheet having a plurality of lines wherein the sheet comprises an x-ray opaque material and is provided in the form of a mesh.

BRIEF DESCRIPTION OF THE DRAWINGS

Further objects and advantages of this invention will be more apparent from the ensuing description when read in conjunction with the accompanying drawings indicating exemplary embodiments of the present invention and wherein.

DETAIL DESCRIPTION OF THE INVENTION

Figure 1:
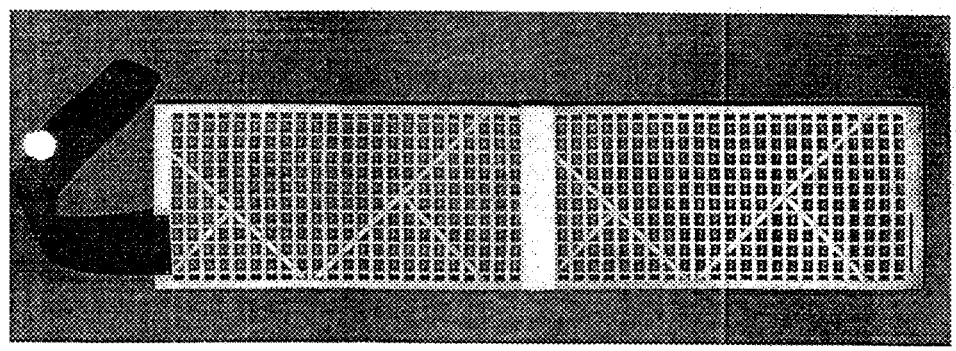
FIG. 1 shows a front view of device according to an embodiment of the invention.

The invention is directed to a device for marking location of organs on skin used with a CAT scan. In exemplary embodiments, the device can be used for CAT scans of the head, for example for use in for neurosurgery. As shown in FIG. 1, the device is made of flexible material, such as a plastic, although other suitable materials readily apparent to persons skilled in the art may be used. The flexible material is impregnated or coated with a x-ray opaque material such as Barium Sulphate, Bismuth Subcarbonate, Bismuth oxychloride, Zirconium oxide, wherein Barium Sulphate is most commonly used material. The invention is not restricted to the use of examples given and other x-ray opaque materials used in the art are understood to be within the scope of the invention. An exemplary flexible material is any bendable or soft plastic such as Low Density Polyethylene. In an exemplary method of making the inventive device x-ray opaque heavy metal substance, such as Barium Sulphate, can be impregnated into the flexible material by mixing with the plastic prior to molding in order to impart radio-opacity. In other embodiments, the x-ray opaque material is coated onto the flexible material after molding.

In one embodiment, the device provides a mesh that creates a plurality of horizontal lines, vertical lines and oblique lines. According to an exemplary embodiment, the horizontal lines (indicated in the figures with letters A-L) are evenly spaced and relatively thin. The vertical lines (indicated with numbering) are also evenly spaced and are thicker than the horizontal lines. To improve the ability to define reference points in the scans resulting from use of the device, thicker vertical lines can be created in regular intervals. For example, in the exemplary embodiment shown in FIGS. 1-3, every fifth vertical line is thicker than intervening four lines. For example, the vertical lines can be spaced at 1 cm intervals and the thicker lines spaced at five cm intervals. Oblique lines can also be present and as illustrated can be provided as thicker lines (relative to the horizontal lines), similar in thickness to the vertical lines. Other patterns can be created that provide accurate regular placement of the reference device. For example, oblique lines may be of different angles and various patterns of thin and thick lines used. Any pattern that improves marking and identifying of location in the CAT scan may be utilized.

Figure 2:
FIG. 2 shows a horizontal cross section of device according to an embodiment of the invention.
Figure 3:
FIG. 3 shows a vertical cross section of device according to an embodiment of the invention.

As also shown in FIGS. 1-3, the device can be rectangular with band. However, other shapes such as circular or elliptical can be used. Various shapes may be used for application to different parts of the body. As illustrated, the device is essentially flat. However, the invention is not limited to such a flat device and can be molded in any suitable shape depending on use and application.

In use, the device is applied externally to the location of body where the CAT scan will be obtained, for example around a head, before taking the CAT scan. Marking accuracy of this device is in the range of +/−5 mm.

Figure 4:
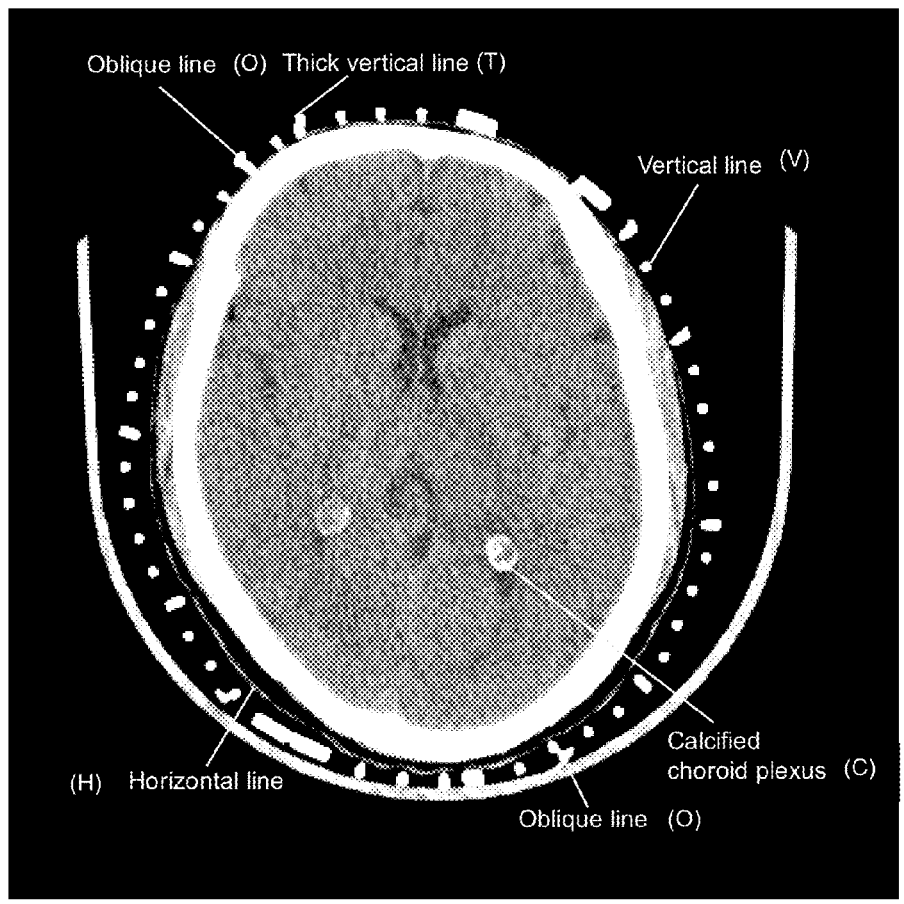
FIG. 4 illustrates a CAT scan of a head obtained with the device on both sides.

A CAT scan taken while utilizing the device according to the invention is illustrated in FIG. 4 indicating the following:
 1. Oblique line (O)
 2. Thick vertical line (T)
 3. Vertical Line (V)
 4. Horizontal line (H)
 5. Oblique line (O)
 6. Calcified choroid plexus (C).

As can be seen, the identifying and marking of a location is apparent and very easy. The position of the oblique lines (O) indicate vertical position and combination of thin vertical lines (V) and thick vertical lines (T) shows horizontal position. Crossing of these two position shows exact location of organ.

For procedures such as surgical & radiotherapy, localizing and marking location of different organs on skin is very important. CAT scan gives rise to a sectional view of organs, but it is difficult to mark location of organs on skin after CAT scan. However, the present invention helps in accurately localizing and marking the organs visible in CAT Scan.

Figure 5:
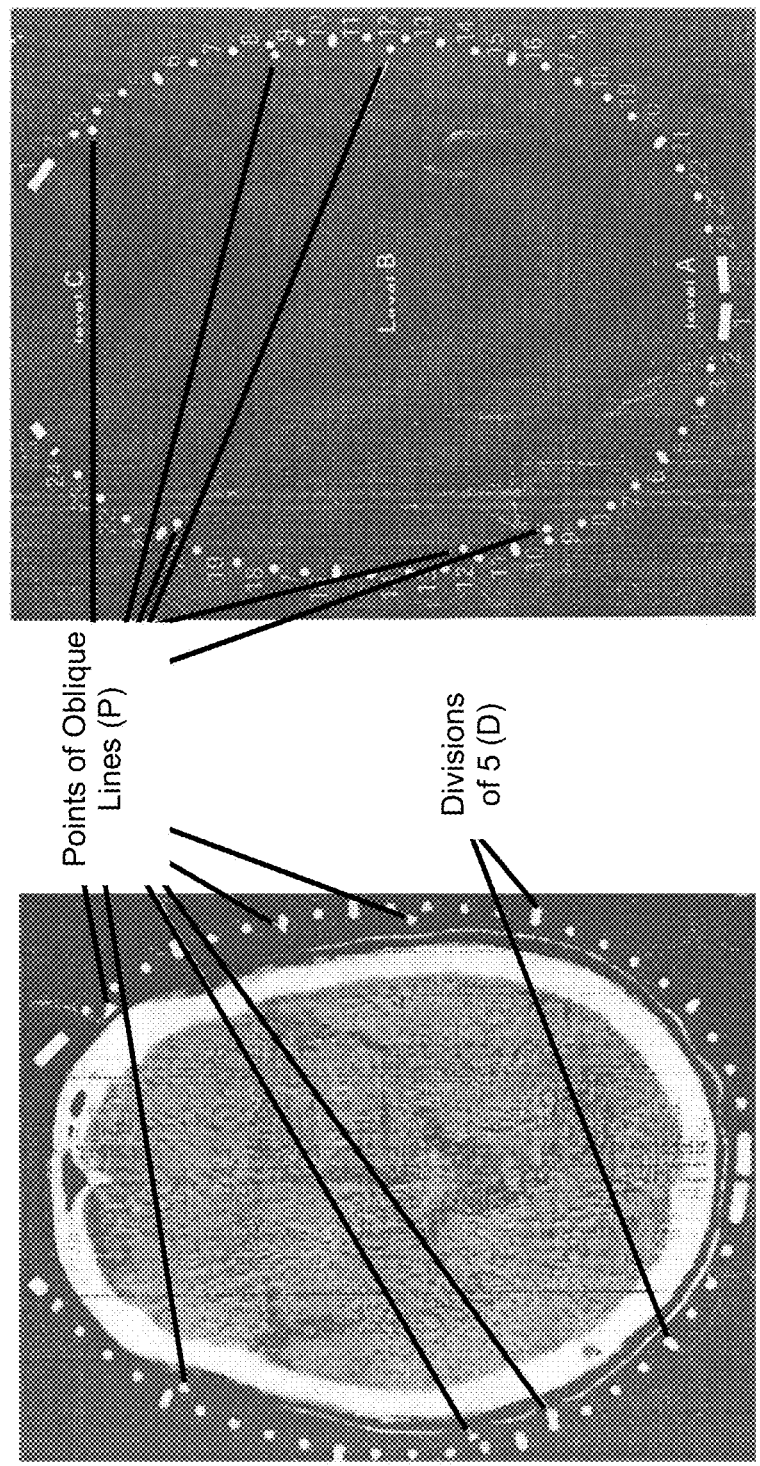
FIG. 5: shows: CAT scan oblique to line of the device.

Device of the instant invention is made of a radio-opaque grid. This grid is visible in CAT scan as dots in a circular manner around the head. The dots are small for each 1 cm and bigger for each 5 cm distance. Further, there is a plurality of dots inside the circle of dots. These dots are of oblique lines. Dots of oblique lines show vertical position. Position of dot of oblique line indicates vertical position of slice. Sometimes the CAT scan may be oblique to line of the device. In this case, vertical position of anterior part and posterior part will be different as shown in FIG. 5 indicating the following:
 1. Points of oblique line (P)
 2. Division of 5 (D)
 3. Level A
 4. Level B
 5. Level C Exemplary Instructions for Application of Device
 1. Apply the device around the head.
 2. Thread hook & loop fastener (or other suitable fastener) through the hole.
 3. Lightly tighten it and press against itself to lock it.
 4. On the front side it should be at the level of lower ridge of frontal bone.
 5. In the middle it should rest on the ear lobule.
 6. To correlate precisely position of device may be marked on skin.
 7. Frontal and side marking.

The above describes craniomapper transverse which is used for transverse section of skull, wherein top of skull is not well defined. Only front, back and sides of skull are covered. Lesions present in vertex area of skull are not visible clearly in the transverse CR scan. To visualize this area, coronal section is required. Therefore, another type of craniomapper is provided, which is called craniomapper coronal. This is used for marking location of lesions in vertex area.

Figure 6:
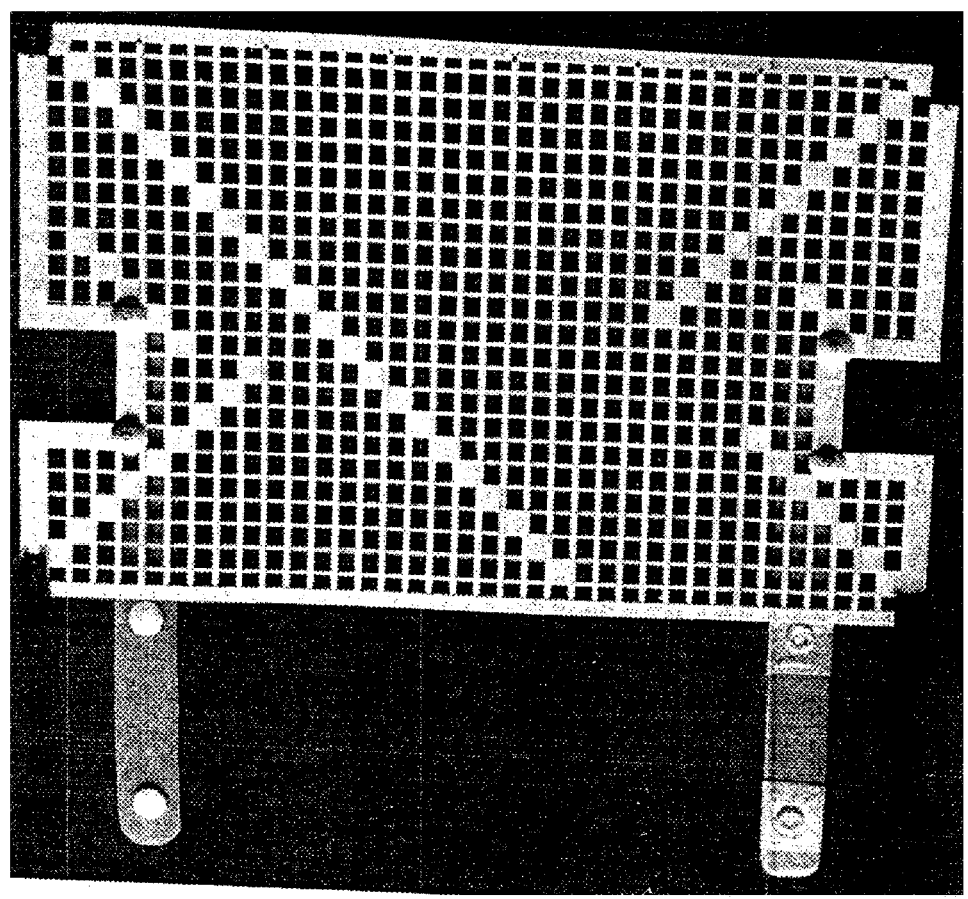
FIG. 6 shows: craniomapper coronal of the present invention.

Said craniomapper coronal is also made of radio-opaque grid. Reference may be made to FIG. 6, wherein the craniomapper coronal is same as craniomapper transverse in terms of construction. However, a cut is provided at two ends for resting on the ears while using.

In said craniomapper coronal, top of skull and sides are well defined, wherein the slices are cut by CT scan parallel to face.

Further, the craniomapper is provided with a plurality of bands as shown in FIG. 6. The bands comprising of back head band and shape band.

Exemplary Instructions for Application of Craniomapper Coronal
 Apply the craniomapper on the head covering top and sides of head.
 Snap join back head band.
 Thread hook and loop fastener through the buckle and fastener
 Join shape band on the front and back side to maintain shape of craniomapper
 On the front side, measure the height of sides of craniomapper from tip of nose with a special scale.
 Make sure to keep position of craniomapper from lobule of ear identical on both sides of head.
 To correlate precisely, position of craniomapper may be marked on side.

Figure 7:
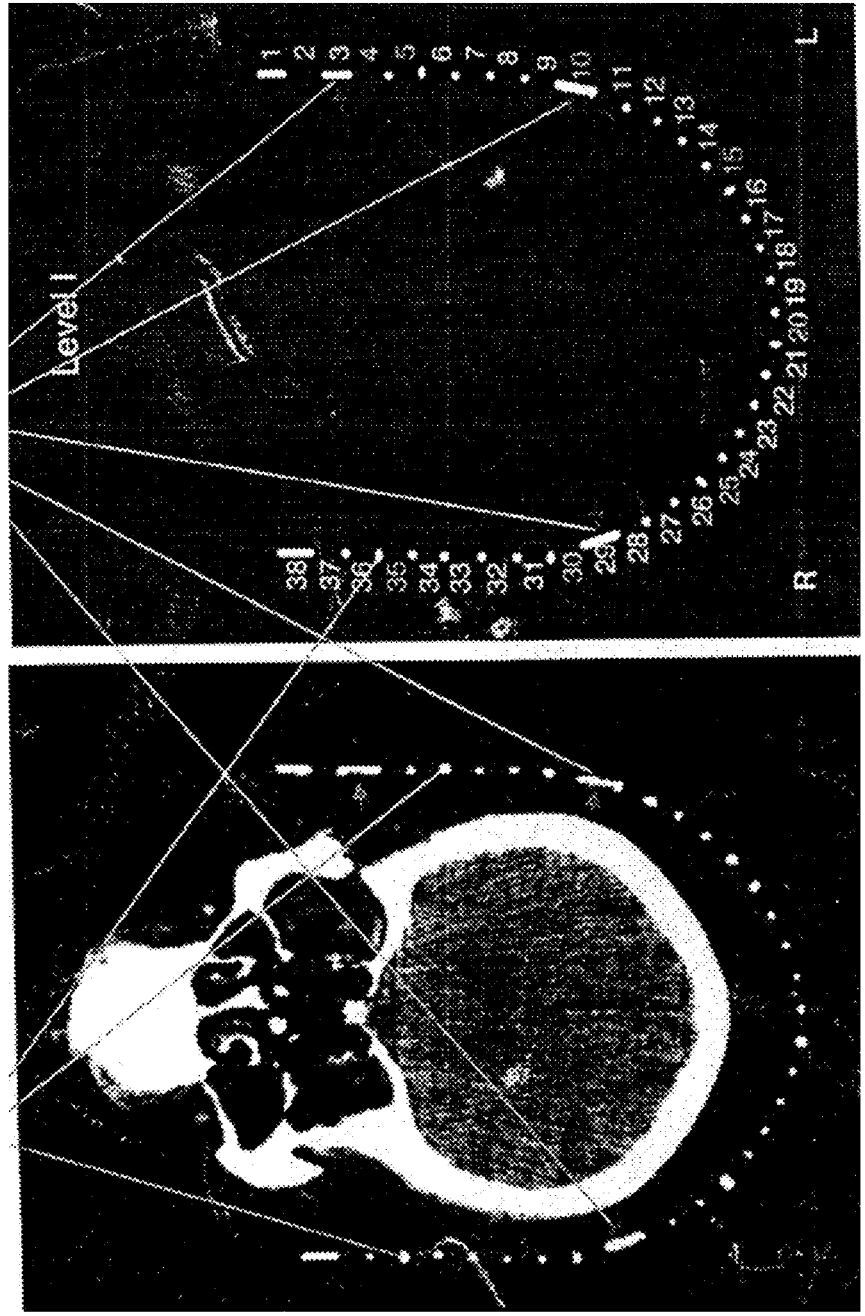
FIG. 7 shows: CAT scan with craniomapper coronal according to the present invention.

Now, reference may be made to FIG. 7 indicating CAT scan using the craniomapper coronal, wherein division of 5 (D) and lines indicating level of section ($L_1$) are shown.

This grid is visible in CAT scan as dots in a circle around the head. The dots are small for each 1 cm and bigger for each 5 cm distance. There are lines between the dots. These lines change position in each section.

Each picture of CT scan is a 2 dimensional picture. Position of lines between dots quantify third dimension. It implies that, in a two dimensional picture third dimension is also present.

Application

For radiotherapy of head, the point of radiotherapy is localized.

For other parts of body: Localization/marking of organs on skin after CAT scan. For ex: fixing the device on chest to mark and localize lung tumors on skin. Here, the device is fixed on body by means of adhesive tapes. Its position is marked on skin with a marker. So that, correlation can be done after CAT Scan.

For surgery of Brain to localize tumors:

The device helps in exact localization of pathology during surgery.

It is to be noted that the present invention is susceptible to modifications, adaptations and changes by those skilled in the art. Such variant embodiments employing the concepts and features of this invention are intended to be within the scope of the present invention, which is further set forth under the claims that follow.

The invention claimed is:

1. A device for identifying the location of internal anatomical features by externally marking skin during a CAT scan, comprising:
    a mesh sheet capable of flexing;
        said mesh sheet having a plurality of lines comprising at least one horizontal line and at least one vertical line; and
        wherein the mesh sheet comprises a material being opaque to x-rays.
2. The device of claim 1, wherein the sheet is a plastic.
3. The device of claim 2, wherein the plastic comprises low density polyethylene.
4. The device of claim 1, wherein said plurality of lines further comprising at least one oblique line.
5. The device of claim 4, wherein the at least one oblique line is thicker than the at least one horizontal line.
6. The device of claim 1, wherein the at least one vertical line is thicker than the at least one horizontal line.
7. The device of claim 1, wherein the at least one vertical line is arranged in a pattern of thick and thin lines.
8. The device of claim 7, wherein every fifth vertical line of the at least one vertical line is thicker than the intervening vertical lines.
9. The device of claim 1, wherein the material is impregnated within the flexible sheet.
10. The device of claim 1, wherein the material is coated on the flexible sheet.
11. The device of claim 1, wherein the material is barium sulphate.
12. The device of claim 1, wherein the sheet is provided with a cut at both ends.
13. The device of claim 12, including a plurality of bands; and
    wherein said plurality of bands comprises a head band and a shape band.
14. A method of identifying the location of an internal anatomical feature during a CAT scan, comprising:
    placing on a surface of a body a mesh sheet comprising a plurality of lines, including at least one vertical line and one horizontal line, and a material opaque to x-rays;
    performing a CAT scan on the body;
    identifying a anatomical feature to be located; and
    identifying a location for the anatomical feature by referencing the sheet.
15. The method of claim 14, wherein the anatomical feature is an organ, a defect, a lesion or a tumor.
16. The method of claim 14, wherein the surface of the body is on a head.

* * * * *

UNITED STATES PATENT AND TRADEMARK OFFICE
CERTIFICATE OF CORRECTION

PATENT NO. : 9,055,915 B2  
APPLICATION NO. : 14/329317  
DATED : June 16, 2015  
INVENTOR(S) : Ghansham D. Agarwal Page 1 of 1

It is certified that error appears in the above-identified patent and that said Letters Patent is hereby corrected as shown below:

Title Page of Patent, should read

(63) Related U.S. Application Data

"Continuation of application No. PCT/IN2013/000414, filed on Jul. 8, 2013, and continuation-in-part of application No. 13/601,170, filed on Aug. 31, 2012."

Signed and Sealed this
Tenth Day of November, 2015

Michelle K. Lee
*Director of the United States Patent and Trademark Office*